United States Patent [19]
Power

[11] Patent Number: 5,546,962
[45] Date of Patent: Aug. 20, 1996

[54] PHYSICAL RESTRAINT DEVICE

[76] Inventor: Michael D. Power, 607 Mountain View #10 Windrift, Park City, Utah 84060

[21] Appl. No.: 487,244

[22] Filed: Jun. 13, 1995

[51] Int. Cl.⁶ ............................. A61B 19/00; A61F 5/37
[52] U.S. Cl. ......................... 128/869; 128/876; 128/878
[58] Field of Search .................................. 128/845, 846, 128/878, 879, 880, 869, 876; 5/495

[56] References Cited

U.S. PATENT DOCUMENTS

| | | | |
|---|---|---|---|
| 794,457 | 7/1905 | Gaiter. | |
| 1,596,792 | 8/1926 | Burry | 128/878 |
| 2,245,293 | 6/1941 | Ogburn | 128/134 |
| 3,027,895 | 4/1962 | Williams | 128/878 |
| 4,071,023 | 1/1978 | Gregory | 128/878 |
| 4,414,969 | 11/1983 | Heyman | 123/133 |
| 4,422,455 | 12/1983 | Olsen | 128/878 |
| 4,558,495 | 12/1985 | Olsen | 24/16 PB |
| 4,580,319 | 4/1986 | Paradis | 24/16 PB |
| 4,628,925 | 12/1986 | Witzel | 128/133 |
| 4,688,564 | 8/1987 | Kelly | 128/878 |
| 4,729,138 | 8/1988 | Heyman et al. | 5/508 |
| 4,854,138 | 8/1989 | Charland | 128/878 |
| 4,910,831 | 3/1990 | Bingold | 128/878 |
| 5,012,821 | 7/1991 | Tarver | 128/876 |
| 5,154,376 | 10/1992 | Baum | 24/16 PB |

*Primary Examiner*—Michael A. Brown
*Attorney, Agent, or Firm*—James L. Sonntag

[57] ABSTRACT

A device for restraining movement without completely prohibiting movement is disclosed. Two coupling devices connected by a extensible material form the physical restraint device. One of the coupling devices may be coupled to a patient while the other may be coupled to a fixed object. The length and extensibility of the extensible material connecting the coupling devices determines the amount of movement allowed between the user and the fixed object. A variety of lengths and strengths of the extensible material may be used and interchanged. Because of the flexibility and extensibility of the material, the physical restraint device may also be used as an exerciser for the person being restrained. A recessed pin locking device is located within each coupling device. Access to each pin locking device is through a hole located in the coupling device. An object such as a pen or a pin must be inserted into the hole in order to release the locking device. When the locking device is released, the coupling device is opened so that it can be connected to or disconnected from the user or fixed object. Because the lock is recessed, access is quick and easy for the person applying the restraint, but is unavailable to the person being restrained.

13 Claims, 3 Drawing Sheets

PHYSICAL RESTRAINT DEVICE

FIELD OF THE INVENTION

The present invention relates to physical restraints. More particularly, the present invention relates to medical and other restraints which restrict yet not prohibit movement.

BACKGROUND ART

In medical situations, some type of restraint for patients is often needed. The amount of restraint necessary, however, typically depends on several factors such as the part of the body needing restraining, the nature of the medical problem, any violent nature of the patient, and strength of the patient. Each of these factors, and more, contribute to deciding how much movement of the patient should be restricted.

For example, confused or disoriented patients who might otherwise leave the health care facility without authorization, or cause harm to themselves or to others, must be confined, either to their beds or to their rooms. Additionally, patients may at times be required to keep their limbs fairly immobile in order for a certain treatment to be successful. Further, with certain patients, restraints are necessary to prevent the patient from having access to medical tubes or other medical apparatus which can be easily pulled out of the body if the patient is not restrained from doing so.

Unfortunately, many of the restraints available today are uncomfortable and unnecessarily confining. Often they do not allow any flexibility in movement. For example, patients may be placed into a tight straightjacket where arm movement is impossible. Or they may be strapped to their beds so tightly that again, any movement is impossible. With these devices, circulation of the immobilized limbs may be impaired, thereby resulting in injury and damage rather than prevention of injury.

Additionally, when the patient is completely immobilized, it is often offensive, degrading, and uncomfortable to the patient. It is also very uncomfortable and traumatic for the relatives and friends of the patient to see the patient harnessed so tightly that normal movement is impossible. The hospital experience, already disturbing, becomes even more so from the sight of distasteful and degrading restraints.

In attempts to solve these problems, devices have been developed which attempt to provide some flexibility for the patient. Typically, the devices consist of straps which at one end encircle a patient's limb, and at the other end is attached to a fixed object such as a bedpost or chair. The length of the strap allows for a limited range of movement. However, these devices still cause discomfort and injury to the patients. When the patient tries to make quick or hard movements past the defined range, the restrained limb is suddenly stopped, and a harsh jarring force is felt against the limb. When the limb being restrained is already injured, the injurious jarring effect is amplified.

Additionally, continuous hard pulling movements against the restraining device may cause a loosening of the device, which may eventually allow the device to become accidentally removed from the patient.

Another problem with the restraint devices used today is the inconvenience of engaging and disengaging the restraints. With the usual strap-type retaining device, buckles or knots are used in order to secure the ends in place around the limbs and around the fixed objects. Because of the inherent awkwardness of buckles and knots, engagement and disengagement of these devices tend to be complicated and time consuming. In emergencies, the straps cannot be easily removed or applied. During the length of time needed for application or removal, injury to the patient could result.

Therefore, several devices were developed which provided more simple methods of release. For example, simple clasping mechanisms were used which could be easily and quickly engaged and disengaged with little time and effort. However, although with these devices the health care worker was able to more easily apply and remove the restraints, unfortunately, the patients were also able to do so. When the devices were such that they allowed a limited range of movement, the patient was often able to reach the clasping mechanism and effect his or her own release.

One solution to this problem was to attach the device to a fixed object so that the clasping mechanism was not within the reach of the patient. For example, some devices attach to the underside of the bed so that the patient will not be able reach the clasping mechanism. However, this position is inconvenient and time consuming for the health care worker. Again, in emergencies, the device cannot be easily and quickly removed. Access of the health care worker to the release mechanism is impeded by the inconvenient and out of the way location of the releasing mechanism.

Another problem with the restraint devices used today is that they are of limited use. The patient is basically restricted to one position in his or her bed or chair. The device cannot be adjusted to provide only a minimal amount of restraint whereby movement around the room would still be possible. Additionally, their use is often complicated and causes an inefficient use of time.

BRIEF SUMMARY AND OBJECTS OF THE INVENTION

In view of the present state of the art, it is an object of the present invention to provide an apparatus for restraining movement which restricts but does not prohibit all movement.

It is another object of the present invention to provide an apparatus for restraining movement which is much more aesthetically pleasing than the restraints currently being used.

It is a further object of the present invention to provide an apparatus for restraining movement which can be used as an exerciser while at the same time restricting certain movements.

It is yet a further object of the present invention to provide an apparatus for restraining movement which can be quickly and easily applied and removed by the person applying the restraint, but cannot be easily removed by the person being restrained.

It is yet another object of the present invention to provide an apparatus for restraining movement which can be easily cleaned and sterilized.

A still further object of the present invention is to provide an apparatus for restraining movement wherein the length of the restraining device can be varied so as to allow or disallow a wide variety of movement as needed.

Yet another object of the present invention is to provide an apparatus for restraining movement which can also be used to restrain movement of inanimate objects such as, for example, luggage.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention is directed to an inventive restraint device which controls but does not totally prohibit a patient's movements. As movement is still allowed, the patient does not feel completely imprisoned and unnecessarily restrained.

The restraining device of the present invention comprises a linking means for linking a user to a fixed object, coupling means for joining the linking means at one end to the user and at the other end to the fixed object, and a locking device for locking the coupling means into place such that the coupling means cannot be removed from the user or the fixed object without releasing the locking device.

The linking means comprises a pliant and extensible material which allows movement between the user and the fixed object. The amount of movement allowed between the user and the fixed object is variable, depending upon the length and extensibility of the linking means. Different lengths of linking means may be used for different purposes.

The locking device is accessible through a hole on the surface of the coupling means. The preferred locking device is recessed such that to release the locking device, an object such as a pen or pin must be inserted into the hole. An advantage of the locking device of the present invention is that access to the locking device is readily available to someone applying the restraint, but is unavailable to the person being restrained. It is simple for the person applying the restraint to be able to insert an object and release the lock, but it would be very difficult for the person being restrained to do so. Thus there is limited risk of the patient being able to release himself or herself from the restraint.

Additionally, keys are not needed with the locking device of the present invention. Therefore, release of the locking device can be done quickly and easily. In emergency situations, time need not be wasted in search of the appropriate key to unlock the restraint.

The coupling means comprises a cylindrical body to which is attached a loop-shaped portion. One end of the loop-shaped portion is pivotally attached to the cylindrical body while the second end of the loop-shaped portion is selectively detachable from the cylindrical body. Attachment and detachment of the loop-shaped portion from the cylindrical body is regulated by the locking device. When the locking device is released, the detachable end of the loop-shaped portion is released from the cylindrical body. This position is referred to as the open position. When the locking device is activated, the detachable end of the loop-shaped portion is locked within the cylindrical body. This position is referred to as the closed position.

When in the open position, the loop-shaped portion of the coupling device can then be connected to a user or to a fixed object. After the loop-shaped portion is closed, the user or fixed object becomes locked within the loop-shaped portion.

When the restraint device within the scope of the present invention is connected to a user at one end and a fixed object at the other end, movement between the user and the fixed object is dependent upon the length and extensibility of the linking means. The more movement allowed, the longer the linking means can be.

As the linking means is formed of a extensible material, the user can move as far from the fixed object as the extensible material will stretch. As the linking means is stretched away from the fixed object, a pulling force pulls the user back towards the fixed object. Therefore, constant pulling away from the fixed object against a pressure pulling back towards the fixed object provides exercise for the patient as well as a protective restraint.

Because movement is allowed between the user and the fixed object to which the user is attached, the patient is also much more comfortable. Circulation is not completely impeded.

Additionally, when using a restraint device wherein movement is restricted yet still allowed, the patient's feeling of imprisonment is much less than when using a device which prohibits all movement.

The present invention is also more aesthetically pleasing that the restraint devices available in the prior art. Because the patient is not completely tied down, it is a less embarrassing and disturbing sight to the friends and relatives of the patient.

Additionally, the present invention can be easily cleaned and sterilized when needed.

And further, the present invention may also be used to restrain inanimate objects such as boxes or luggage.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The present invention relates to physical restraints. More specifically, the present invention relates to physical restraints used in health care facilities for restricting, yet not prohibiting, movement.

The physical restraint device within the scope of the present invention may also be used for many purposes outside of the medical field. However, the main use of the physical restraint device, its use in health care facilities, will be primarily discussed as the preferred embodiment.

Figure 1:
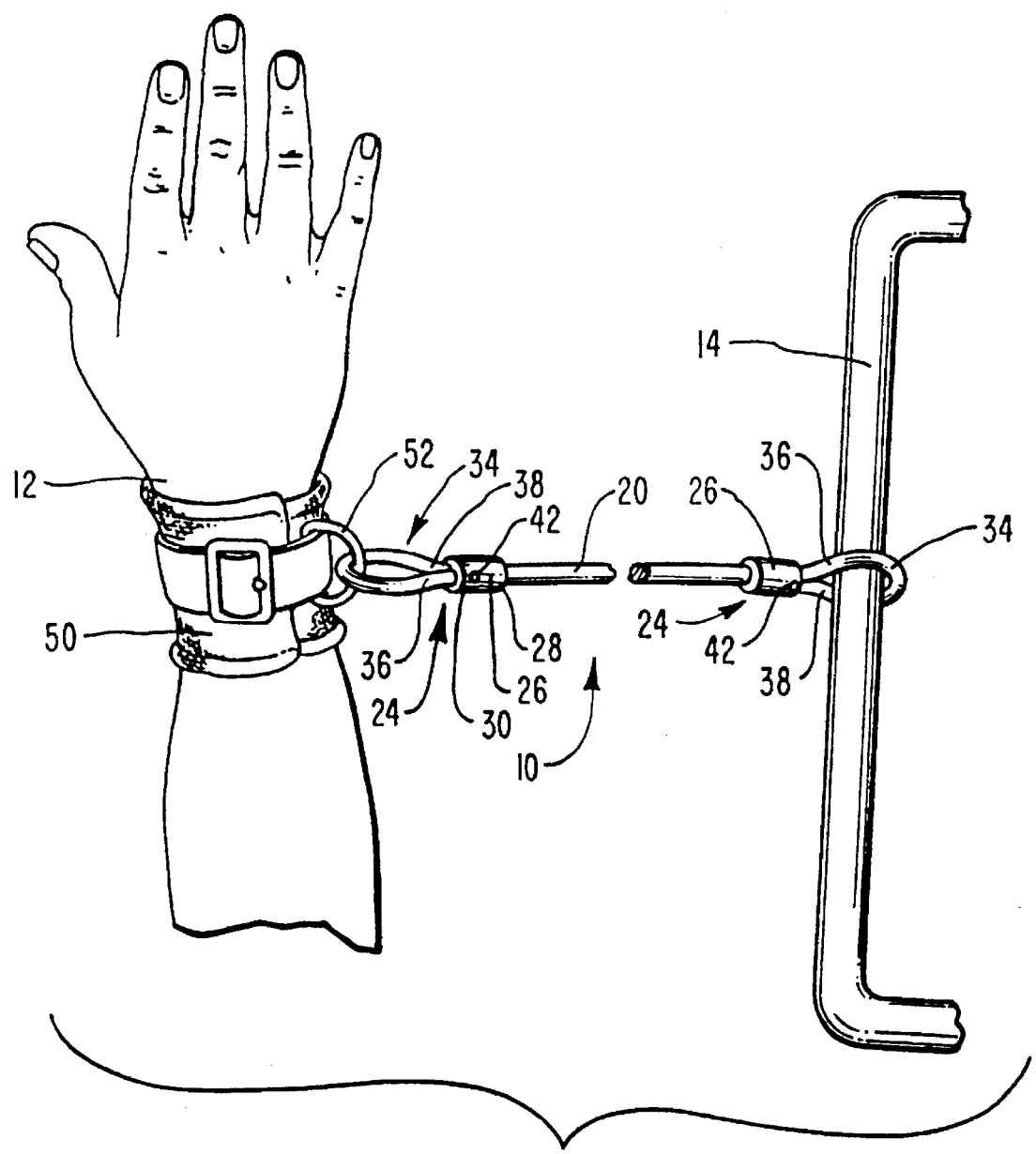
FIG. 1 is a perspective view of a presently preferred embodiment of the physical restraint device within the scope of the present invention.

With reference now to the Figures, the preferred embodiment of the restraint device is illustrated in FIG. 1 and generally labelled as 10. The restraint device 10 can be used to restrict the movement of a user by linking the user to a fixed object and allowing only limited movement between the user and the fixed object.

Any portion of the user's body can be restrained by the restraint device 10. For example, as illustrated in FIG. 1, movement of a user's arm may be controlled by linking the user's arm to a fixed object such as a bed rail.

As shown in FIG. 1, the wrist 12 of the user may be attached by restraint device 10 to a bed railing 14. A linking means for linking the user to the fixed object, stretches between the user and the fixed object. The distance which wrist 12 can move away from bed railing 14 while attached by the restraint device, is dependent upon the length and extensibility of the linking means.

The linking means comprises a pliant, extensible material for linking the user to the fixed object. The extensibility of the linking means permits a varying degree of movement between the user and the fixed object. Using the preferred embodiment of FIG. 1 as an example, the wrist 12 may move as far away from bed railing 14 as the linking means can stretch. When the linking means reaches the limit of its stretching, further movement is prohibited. If allowance of less movement is desired, the linking means can be shortened.

In the preferred embodiment within the scope of the present invention as shown in FIG. 1, linking means comprises a length of surgical tubing 20. The standard surgical tubing used in most health care facilities having a ¼ inner diameter is preferred. However, surgical tubing with other widths, or other extensible material, is also within the scope of the present invention.

Determination of the length of the surgical tubing to be used with the physical restraint device may depend upon each particular type of use and the amount of movement desired. A longer length will allow for more movement between the user and the bed railing. A shorter length will allow less movement and will provide more restriction. For example, the restraint may be used to prevent the patient from removing any uncomfortable but necessary medical apparatus from his or her body. The surgical tubing for this purpose should be made a length such that the patient can move his or her arm fairly freely, but cannot reach the main area where the medical apparati are situated. As an example, the length should allow the patient substantial arm movement, but should prohibit the patient from being able to reach and remove necessary oxygen or feeding tubes or the like from the patient's body.

Additionally, if the patient has received some type of treatment and is not allowed to move a particular limb past a certain distance, the tubing should be of a length such that even when stretched, the limb cannot move past that distance. This device acts as a gentle reminder for the patient to move their limbs only as allowed.

Another advantage of the extensible linking means used within the scope of the present invention is that it restricts movement gently and not with the harsh effects of the prior art. When the user reaches a spot where movement is no longer allowed, the extensible linking means gently pulls back upon the user's limb. If the user were to suddenly jerk his or her limb away, the linking means would stretch to accommodate the hasty movement rather than jarring the patient's limb with a harsh force. This is an advantage over many non-extensible prior art devices used today which cause a jarring force when the limb is suddenly moved out of range of the device. When the jarred limb is also an injured limb, the jarring effect of the prior art device is amplified.

A further advantage of the extensible linking means is the exercise provided by the stretching capability of the linking means. When the patient's limb moves away from the fixed object and moves past the relaxed length of the linking means, the linking means applies a pressure on the limb. The more the limb pulls away, the greater the pressure of the linking means pulling the limb back. Repetition of these movements exercises the limb and discourages muscular atrophy and lack of circulation.

Again, the length of the linking means can be adjusted to fit the extent and amount of exercise desired.

Another element of the present invention comprises a coupling means for joining one end of the linking means to the user and the other end of the linking means to the fixed object, so that the user and the fixed object are linked.

Referring back to FIG. 1, it can be seen that a coupling means for joining one end of the linking means to the user and the other end of the linking means to the fixed object is attached at each end of the linking means 20. An example of an appropriate coupling means is illustrated in greater detail as coupler device 24 in FIGS. 2 and 3.

The coupler device 24 comprises a cylindrical body 26 having a first end 28 and a second end 30. First end 28 is connectable to the linking means in such way that the linking means is held securely by the cylindrical body 26 even when linking means is stretched tightly and pulled away from the cylindrical body.

Figure 4:
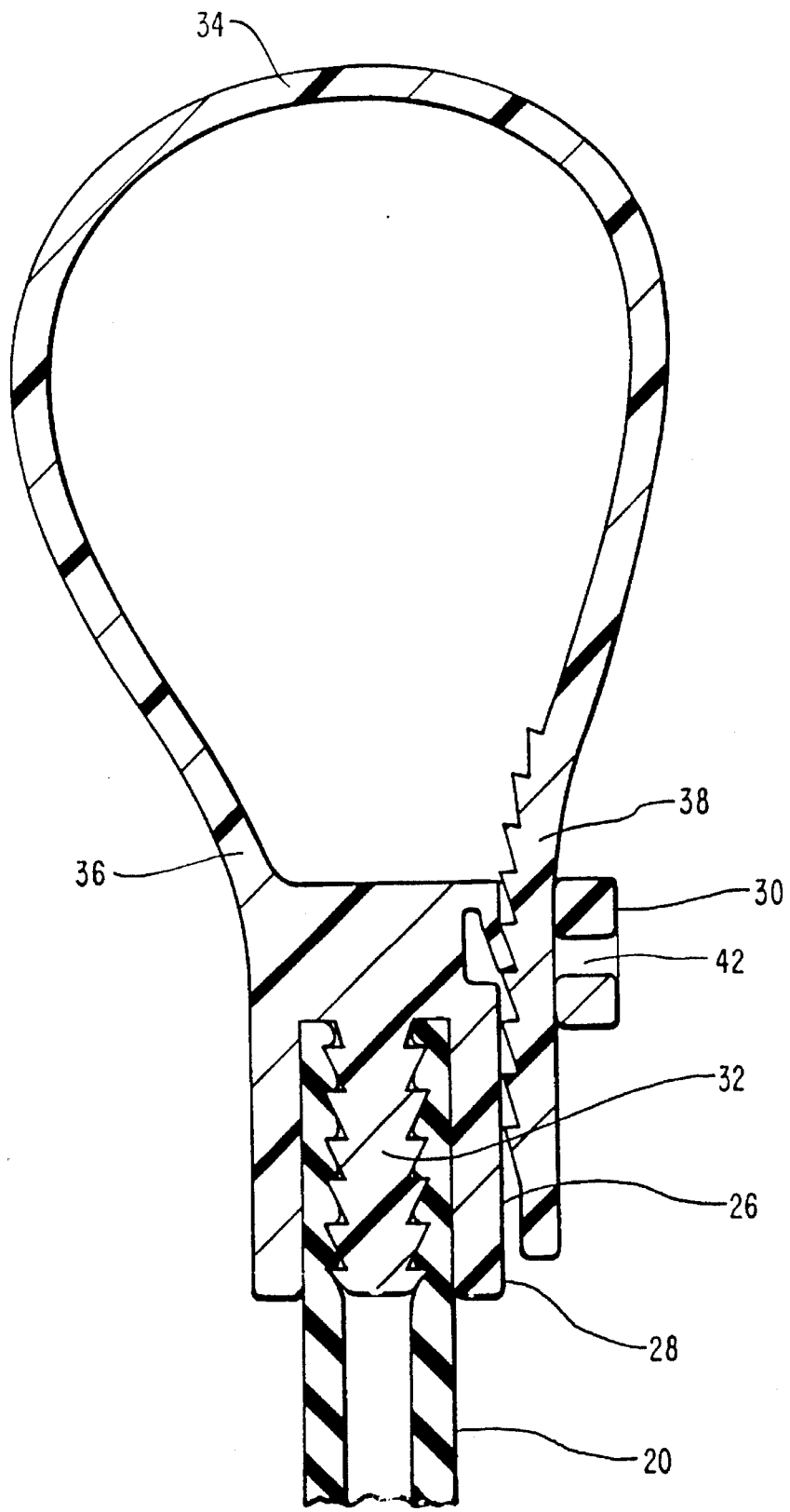
FIG. 4 is a cross-sectional view along the line 4—4 of FIG. 3 illustrating the ridged projection within the coupling device.

Connecting means for connecting the linking means with the cylindrical body and securing the linking means therein, is located within the cylindrical body. In the preferred embodiment as illustrated in FIG. 4, the connecting means comprises a ridged projection 32 within cylindrical body 26 onto which the surgical tubing 20 is attached. Ridges encircle and extend outwardly from the ridged projection 32 so as to provide a grip for the surgical tubing 20.

For use of the preferred embodiment wherein the linking means comprises surgical tubing, one end of the rubber surgical tubing is inserted into the cylindrical body 26 and over the ridged projection 32. The outwardly extending ridges on the ridged projection 32 grip the rubber surgical tubing tightly, in such way that the more firm the rubber surgical tubing is pulled, the more securely it is held by the ridged projection 32 within the cylindrical body 26.

Upon desire of the person applying the physical restraint device, the surgical tubing can be disconnected from the ridged projection 32. An advantage of this is that one pair of the coupling means may be used with many different lengths of surgical tubing and for many different uses. The length of the surgical tubing to be used may be easily changed with each different need for restraint. The ridged tubing may also be changed after each use if necessary.

For example, if only a very little movement should be allowed, a short piece of surgical tubing should be connected to the coupling means. If more mobility can be allowed, a longer portion of surgical tubing may be attached. (Of course the amount that the extensible material will stretch must also be taken into account when planning particular lengths of tubings to be used.)

It can be appreciated that other means for connecting the linking means with the cylindrical body and holding the linking means therein is also within the scope of the present invention.

A loop-shaped portion 34 having a fixed end 36 and a detachable end 38 extends outwardly from the second end 30 of the cylindrical body 26. Fixed end 36 of the loop-shaped portion 34 is pivotally attached to second end 30. Detachable end 38 of loop-shaped portion 34 can be selectively attached to or detached from second end 30.

Figure 2:
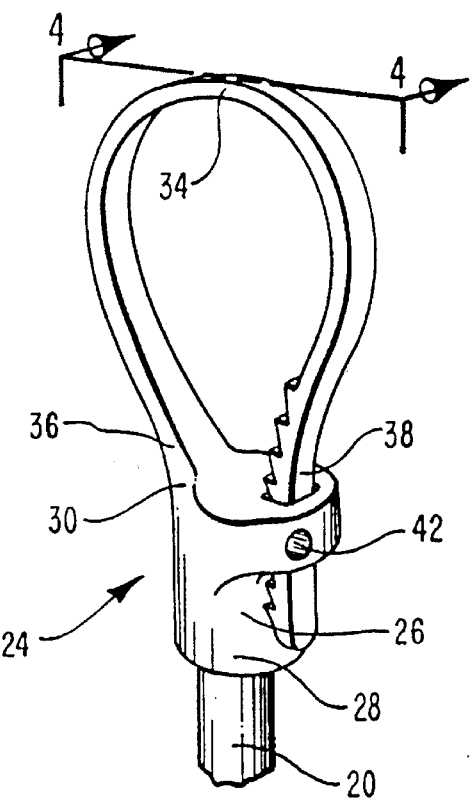
FIG. 2 is a perspective view of the coupling device of the present invention.
Figure 3:
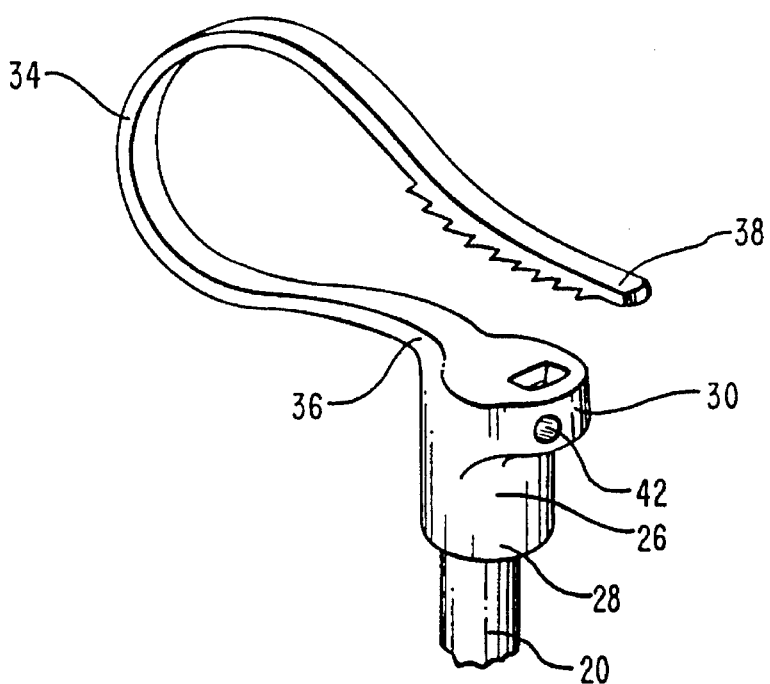
FIG. 3 is a perspective view of the coupling device of FIG. 2 in the open position.

As shown in FIG. 2 and 3, loop-shaped portion 34 is capable of being in a closed or an open position. In the closed position of FIG. 2, fixed end 36 and detachable end 38 of loop-shaped portion 31 are both in secure contact with second end 30 of cylindrical body 26. In the open position as illustrated in FIG. 3, detachable end 38 is positioned away from second end 30 of cylindrical body 26 and the loop-shaped portion 34 is pivoted away from second end 30 by the pivotal attachment at fixed end 36. While in this open position, loop-shaped portion 34 can be positioned around a fixed object or a user. Then, when loop-shaped portion 34 is closed, the fixed object or the user will be locked within the loop.

In the preferred embodiment, loop-shaped portion 34 is constructed of a plastic material which is strong enough to withstand the pulling forces of a restrained patient yet simple and easy to manufacture. In other embodiments, the loop-shaped portion may be comprised of a metal material or other strong material.

In one embodiment within the scope of the present invention, the detachable end 38 may be used to assist in holding the surgical tubing onto the ridged projection. Detachable end 38 may be formed such that when loop-shaped portion 34 is in the closed position, the detachable end 38 contacts and rests against the surgical tubing, thereby securing it against the ridged projection. When loop-shaped portion 34 is opened, the pressure against the surgical tubing is released, and the surgical tubing may be removed and replaced if wished.

A locking means for locking the coupling means into place such that the coupling means, once attached to the user of the fixed object, cannot be removed from the user or the fixed object without release of the locking means, is another important element of the present invention. The locking means is located within the coupling means such that access to the locking means is unavailable to the user being restrained, yet readily available to the person applying the restraint.

The locking means controls whether loop-shaped portion is in the open or closed position. The locking means holds detachable end 38 in the closed position until the locking means is released. When the locking device is released, detachable end 38 is released from second end 30 and the loop-shaped portion 34 is placed into the open position.

In the preferred embodiment, as seen in the cross-section of FIG. 4, the locking means comprises a recessed pin locking device 42 located within cylindrical body 26. The recessed pin locking device 42 is accessed through a small hole located in the cylindrical body. To release the recessed pin locking device 42, an object such as a pen or pin must be inserted into this small hole. As the object is inserted into the hole, the object contacts the recessed pin of the locking device and thereby releases the locking device. Release of the recessed pin locking device 42 causes the detachable end 38 to be released from the cylinder body 26. This places loop 34 into the opened position.

An important advantage to having a recessed pin locking device 42 is the denied access to the patient. While it would be simple for a health care worker to be able to insert an object and release the lock, it would be very difficult for the person being restrained to do so. This is an advantage over many prior art devices.

With many of the prior art devices, if the patient is given any room for movement, there is a risk that the patient would be able to reach over and untie, unbuckle or undo the restraint device. Therefore, the patient must be held tightly by the restraint with only little movement allowed. This leads to problems like impeded circulation, muscle atrophy and bed sores, as discussed earlier.

With the recessed pin locking device 42 of the present invention, the patient is allowed movement during the period of restraint. Since the lock is recessed and can be released only by insertion of an object into the entry hole, the danger of a patient releasing his or her own restraints is decreased.

Another advantage of the recessed pin locking device 42 of the present invention is its quick release system. Sometimes there will be emergencies where the restraint device must be released immediately. With many of the prior art devices, a key is needed to unlock the restraint devices. Unfortunately, it may be difficult to quickly and easily find the appropriate keys during emergencies. By the time the correct key is produced and used to release the patient, the patient may already have injured himself or herself.

For example, if the patient were to have a heart attack while under restraint, the restraints may first have to be removed before treatment for the heart attack can be administered. If time is wasted in removing the restraints, the patient could either die or become irreversibly debilitated. Therefore, a reliable restraint device such as the present invention which is quickly releasable by the health care worker but not by the patient is very advantageous.

Other types of locking means which cannot easily be released by the patient but which can easily be released by the health care worker can also be used within the scope of the present invention.

Loop-shaped portion 34 is attached to a patient through the use of restraints known in the art. In FIG. 1, the preferred wrist collar used in conjunction with the present invention is illustrated. The preferred wrist collar, a Posy wrist restraint, comprises a soft collar encircling the wrist and having a "D" ring 52 located thereon. When in the open position, loop-shaped portion 34 of coupler device 24 can be inserted through D ring 52, thereby connecting the patent to the physical restraint device. Similar or equivalent collars can be used for connection of the coupler device to other parts of the user's body.

Once the physical restraint device is coupled to both the user and to the fixed object, the user is restrained. Allowable movement is limited to the distance to which the linking means can stretch.

The inventive physical restraint device may be used to restrain patients in several different ways. As earlier discussed, the arm of the patient may be restrained to the bed rail. The legs of the patient may be restrained in a similar manner. It is also conceivable that the patient may be restrained around the waist area to prevent the patient from rotating in bed. Other methods of restraining the patient are also available.

The restraint device within the scope of the present invention may also be used in many other ways. For example, the restraint may be used as an exerciser. As the user pulls his or her limb away, the restraint device exerts opposite tension and pulls the user's limb back. Repetition of these movements provides exercise to the restrained limb.

The restraint may also be used as a gentle reminder against movement. For example, if it is preferred that the patient lay supine, the coupler devices may be joined to the bed railings on each side of the bed. Each time the patient tries to sit up, he or she will feel the pressure of the linking means against his or her chest and will be reminded to remain in a horizontal position.

Further, the restraint device within the scope of the present invention can be used to restrict movement into and out of rooms. For example, there are instances when wheelchair bound patients are restricted to their rooms or the immediate area. In order to keep the unwilling patients inside or around their rooms, the health care workers are forced to either watch the patients very carefully, or lock the patients into their rooms. Both choices are inconvenient and undesirable. With the present invention, however, the patient can be restricted to the room without constant supervision and without the patient feeling completely imprisoned.

For use in this manner, one coupling means may be attached to a fixed object within the patient's room. The second coupling means may be attached to the back of the wheelchair. The linking means can be made of whatever length desired. Thus, depending upon the length of the linking means, the patient could be allowed free access to the entire room, but would be allowed out of the room only as far as allowed by the length and stretching capability of the linking means. The length of the linking means would correspond to the distance the patient is allowed to move outside of the room. Since the coupling means would be attached to the back of the wheelchair, the patient would not have access to it and would not be able to release the locking mechanism without assistance. Therefore, the patient is secure yet not immobilized.

It is conceivable that the present invention could also be used to restrain walking patients to their rooms. In nursing homes, many of the less lucid patients tend to wander around and outside the buildings. Often there are simply not enough health care workers available to individually watch each patient at all times. Therefore, with the patients who are especially inclined to wander away from their rooms and possibly cause injury to themselves or others, the present invention can be used to restrict their movements. Specifically, one coupling means could be linked with a fixed object either within the patient's room, at the nurse's station, or at whatever area to which the patient is being confined. The other coupling means could be linked directly to the patient. This could be done through the use of a waist restraint, wrist restraint, or some other comparable restraint to which the coupling means could be linked. The patient could then wander around, but would be limited to that area within the reach of the linking means. The patient would retain some sense of freedom while still being restricted for safety reasons.

It is within the scope of the present invention to be used for non-medical purposes as well. The same device could be used, for example, to secure luggage to the top of a car. On those cars having luggage carriers built onto their roofs, the restraint device could stretch across the width of the car, with the coupling means attached to the bars of the luggage carriers. Luggage could be securely tied down by the restraint device of the present invention.

The device of the present invention may also be used for exercising.

Cylindrical body 26 may be manufactured in different ways. For example, the cylindrical body 26 may be easily molded in one piece with the ridged projection molded therein. The loop-shaped portion 34 may be molded in one piece with the cylindrical body, or separately and attached at a later time. Because the material is an inexpensive plastic, many of the coupler devices may be made economically. Additionally, the restraint devices may be easily cleaned and sterilized between each use if necessary.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States patent is:

1. A device for physically restraining movement comprising:

a) linking means for linking a user to a fixed object, the linking means having two ends and being pliant and extensible such that movement between the user and the fixed object is limited but not restricted, and such that the distance between the user and the fixed object is variable, the variability depending upon the length and extensibility of the linking means;

b) coupling means, attached at each end of the linking means and attachable to the user or the fixed object, for joining one end of the linking means to the user and the other end to the fixed object; and c) a locking means for locking the coupling means into place such that the coupling means, once attached to the user of the fixed object, cannot be removed from the user or the fixed object without release of the locking means, the locking means being located within the coupling means such that access to the locking means is unavailable to the user being restrained, yet readily available to the person applying the restraint.

2. A device as defined in claim 1, wherein the linking means comprises a length of surgical tubing.

3. A device as defined in claim 1 wherein the length of surgical tubing has a ¼ inch inner diameter.

4. A device as defined in claim 1, wherein the coupling means comprises:

a) a cylindrical body having a first end and a second end, the first end being connectable to the linking means; and b) a loop-shaped portion having a fixed end and a detachable end and extending from the second end of the cylindrical body, the detachable end being detachable from the cylindrical body in such way that the detachable end is detached from the cylindrical body when the loop-shaped portion is in an opened position and the detachable end is connected to the cylindrical body when the loop-shaped portion is in a closed position, and the fixed end of the loop-shaped portion being pivotally attached to the cylindrical body.

5. A device as defined in claim 4, wherein the loop-shaped portion of the coupling means is configured such that when the loop-shaped portion is in the closed position, the detachable end contacts and rests against the linking means, thereby assisting and securing the attachment of the linking means to the cylindrical body.

6. A device as defined in claim 4, wherein the cylindrical body comprises a plastic material.

7. A device as defined in claim 4, wherein the cylindrical body comprises a metal material.

8. A device as defined in claim 4, wherein the loop-shaped portion comprises a plastic material.

9. A device as defined in claim 4, wherein the cylindrical body further comprises a ridged projection located within the cylindrical body, the ridged projection attachable to the linking means in order to secure the linking means to the cylindrical body.

10. A device as defined in claim 4, wherein the coupling means comprises:

a) a cylindrical body having a first end and a second end, the first end being connectable to the linking means; and b) a loop-shaped portion having a fixed end and a detachable end and extending from the second end of the cylindrical body, the detachable end being detachable from the cylindrical body, and the fixed end of the loop-shaped portion being pivotally attached to the cylindrical body.

11. A device as defined in claim 1, wherein the locking mean comprises a recessed pin locking device.

12. A device for physically restraining movement comprising:

a) rubber surgical tubing for linking a user to a fixed object, the surgical tubing having two ends and being pliant and extensible such that movement between the user and the fixed object is limited but not restricted, and such that the distance between the user and the fixed object is variable, depending upon the length and extensibility of the surgical tubing;

b) coupling means, attached at each end of the linking means and attachable to the user of the fixed object, for joining the linking means to the user at one end and to the fixed object at the other end;

c) a recessed pin locking device for locking the coupling means into place such that the coupling means cannot be removed from the user or the fixed object without activation and release of the locking device, the locking device being located within the coupling means such that access to the locking means is denied to the user being restrained, yet readily available to the person applying the restraint.

13. A device for physically restraining movement comprising;

(a) linking means for linking a user to a fixed object, the linking means having two ends and being pliant and extensible such that movement between the user and the fixed object is limited but not restricted, and such that the distance between the user and the fixed object is variable, the variability depending upon the length and extensibility of the linking means;

(b) coupling means attached at each end of the linking means and attachable to the user or the fixed object, for joining the liking means to the user at one end and the fixed object at the other end;

(c) a recessed pin locking device for locking the coupling means into place such that the coupling means cannot be removed from the user of the fixed object without activation and release of the locking device, the recessed pin locking device comprising a pin that when pressed by an object activates and releases the locking device, the pin being recessed in a hole in the coupling means such that it is accessible only by insertion of the object through the hole.

* * * * *